United States Patent
Yoda et al.

(10) Patent No.: US 10,189,999 B2
(45) Date of Patent: Jan. 29, 2019

(54) RESIN COMPOSITION FOR COATING AGENT, MOLDED ARTICLE, AND IMAGE DISPLAY DEVICE

(71) Applicant: JNC CORPORATION, Tokyo (JP)

(72) Inventors: Akiko Yoda, Chiba (JP); Koji Ohguma, Tokyo (JP); Mikio Yamahiro, Chiba (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 15/300,793

(22) PCT Filed: Mar. 31, 2015

(86) PCT No.: PCT/JP2015/060247
§ 371 (c)(1),
(2) Date: Sep. 30, 2016

(87) PCT Pub. No.: WO2015/152288
PCT Pub. Date: Oct. 8, 2015

(65) Prior Publication Data
US 2017/0015834 A1     Jan. 19, 2017

(30) Foreign Application Priority Data

Mar. 31, 2014   (JP) ................................ 2014-074664

(51) Int. Cl.
*C09D 4/06*       (2006.01)
*C07F 7/08*       (2006.01)
(Continued)

(52) U.S. Cl.
CPC .............. *C09D 4/06* (2013.01); *C07F 7/0838* (2013.01); *C08G 77/20* (2013.01); *C08G 77/388* (2013.01);
(Continued)

(58) Field of Classification Search
None
See application file for complete search history.

(56) References Cited

U.S. PATENT DOCUMENTS

2012/0207990 A1* 8/2012 Akutagawa .......... C09D 135/02
428/213

FOREIGN PATENT DOCUMENTS

JP     2001-201723     7/2001
JP     2003096400      4/2003
(Continued)

OTHER PUBLICATIONS

Machine English translation_WO_2006109496_A1; Yamada, Yasuharu; Radiation Curable Resin Composition and Antireflection Coating; EPO; whole document.*

(Continued)

*Primary Examiner* — Tahseen Khan
(74) *Attorney, Agent, or Firm* — JCIPRNET (57) ABSTRACT

A compound capable of increasing the scratch resistance of, for instance, a hard-coat agent and a resin composition for a coating agent containing the compound are shown. The resin composition for a coating agent of the present application contains: a silicon compound (a) represented by formula (I) of the specification; and a curable resin (b). In formula (I), $R_1$ is a $C_3$ or $C_4$ alkylene group, and X is a group represented by formula (II) of the specification having a urethane skeleton and having a (meth)acryloyl group at an end. In formula (II), $R_2$ is hydrogen or a methyl group, and n is an integer of 0 or 1. The molecular weight of the silicon compound (a) is 500 to 699.

5 Claims, 1 Drawing Sheet (51) Int. Cl.
  *C09D 201/00* (2006.01)
  *C09D 183/08* (2006.01)
  *C08G 77/20* (2006.01)
  *C08G 77/388* (2006.01)
  *G02B 1/14* (2015.01)
  *C08J 3/28* (2006.01)
  *C08J 7/04* (2006.01)

(52) U.S. Cl.
  CPC ............... *C08J 3/28* (2013.01); *C08J 7/047* (2013.01); *C09D 183/08* (2013.01); *C09D 201/00* (2013.01); *G02B 1/14* (2015.01); *C08J 2383/08* (2013.01)

(56) References Cited

FOREIGN PATENT DOCUMENTS

| | | |
|---|---|---|
| JP | 2006-290696 | 10/2006 |
| JP | 2009-249558 | 10/2009 |
| JP | 2010-138255 | 6/2010 |
| JP | 2010138255 A1 * | 6/2010 |
| JP | 2013-023547 | 2/2013 |
| JP | 2013-154631 | 8/2013 |
| TW | 200700443 | 1/2007 |
| WO | 2006/109496 | 10/2006 |
| WO | WO2006109496 A1 * | 10/2006 |

OTHER PUBLICATIONS

Machine English translation_JP_2010138255_A; Tokunaga, Y.; Polyether-Modified Polysiloxane Compound and Radiation Curable Composition Containing the Same; Jun. 24, 2010; EPO and Derwent; whole document.*

"International Search Report (Form PCT/ISA/210) of PCT/JP2015/060247", dated Jun. 30, 2015, with English translation thereof, pp. 1-4.

"Office Action of China Counterpart Application," with partial translation thereof, dated Apr. 19, 2018, p. 1-p. 9.

"Office Action of Japan Counterpart Application," with English machine translation thereof, dated Oct. 30, 2018, pp. 1-6.

* cited by examiner

RESIN COMPOSITION FOR COATING AGENT, MOLDED ARTICLE, AND IMAGE DISPLAY DEVICE

CROSS-REFERENCE TO RELATED APPLICATION

This application is a 371 application of the international PCT application serial no. PCT/JP2015/060247, filed on Mar. 31, 2015, which claims the priority benefit of Japan application no. 2014-074664, filed on Mar. 31, 2014. The entirety of each of the abovementioned patent applications is hereby incorporated by reference herein and made a part of this specification.

BACKGROUND OF THE INVENTION

Field of the Invention

The invention relates to a resin composition for a coating agent, and more particularly, to a resin composition for coating significantly increasing scratch resistance.

Description of Related Art

In recent years, portable liquid crystal display (LCD) terminals that can be used outdoors have become very popular, and examples include mobile terminals such as smart phones, personal navigation devices (PND), or wearable displays such as Google glasses.

These products are used while being carried, and therefore need to be lightweight, and as a result some of the glass components are replaced by plastic. However, plastic (in particular polyethylene terephthalate (PET), polycarbonate (PC), polymethyl methacrylate (PMMA), cycloolefin . . . etc.) has the properties of lightweight and high transparency, but lacks scratch resistance. A general means for solving the issue includes a surface treatment using a hard-coat agent to prevent scratching.

As a method to prevent scratching, patent literature 1 discloses a coating agent for glass substrates having excellent scratch resistance and excellent adhesion with glass and anti-dispersion (paragraph 0019). Patent literature 2 discloses a laminate body having repair function for deep scratches and a self-repair layer continuously performing repair function (paragraph 0004). Damage repair is performed via the following method: a coating solution formed by mixing a thermoplastic resin in an active energy ray curable resin is coated on a substrate layer such that the active energy ray curable resin is cured and a coating is formed, the damaged coating is heated, and the damage is buried by softening the thermoplastic resin in the coating (paragraph 0005). Patent literature 3 discloses a photocurable resin composition including a dimethyl silicone (meth) acrylate oligomer. However, the object thereof is waterproofing and it is used as a functional screen, and transparency or low haze desired for a display are not considered. Moreover, the focus thereof is prolonged water repellency or lubricating properties, and scratch resistance of the coating obtained from stress relief and such is not considered (claim 1, paragraph 0008).

CURRENT TECHNICAL LITERATURE

Patent Literature

[Patent literature 1] JP 2006-290696
[Patent literature 2] JP 2013-154631
[Patent literature 3] JP 2013-023547

SUMMARY OF THE INVENTION

Issue to be Solved by the Invention

High scratch resistance is required for the coating agent or laminate body above.

Therefore, the invention provides a compound capable of increasing the scratch resistance of, for instance, a coating agent and a resin composition containing the compound for a coating agent.

Means for Solving the Issue

The Inventors discovered that, if a compound (silicon compound) formed by modifying the two ends of a silicone compound by acrylic acid is added in a hard-coat agent, then the scratch resistance is significantly increased, and the invention is thus achieved. Moreover, "modified by acrylic acid" refers to introducing a (meth)acryloyl group to a compound.

The resin composition for a coating agent of the first example of the invention includes: a silicon compound (a) represented by formula (I); and a curable resin (b); in formula (I), $R_1$ is a $C_3$ or $C_4$ alkylene group, X is a group represented by formula (II) having a urethane skeleton and a (meth)acryloyl group at an end, and in formula (II), $R_2$ is hydrogen or a methyl group, n is an integer of 0 or 1, and the molecular weight of the silicon compound (a) is 500 to 699.

In this way, the silicon compound (a) can be mixed in the curable resin with good compatibility. Therefore, a coating agent significantly increasing scratch resistance can be obtained. The reason is that: the silicone skeleton (siloxane bond) in the silicon compound (a) has lubricity, mold-release properties, flexibility (softness), and if the silicon compound (a) and the curable resin are used together, then scratch resistance thought to be obtained by stress relief can be significantly increased.

The resin composition for a coating agent of the second example of the invention is the resin composition for a coating agent of the first example of the invention, wherein the curable resin (b) is a UV curable resin having at least one (meth)acryloyl group.

In this way, via UV irradiation, the (meth)acryloyl group of the silicon compound (a) and the (meth)acryloyl group of the curable resin (b) can be bonded to fix the silicon compound (a) on the curable resin (b).

The molded article of the third example of the invention has a cured product formed by curing the resin composition for a coating agent of the first example or the second example of the invention; and a substrate covered by the cured product.

In this way, the surface of the substrate can be protected by the cured product formed by curing the resin composition for a coating agent, and the scratch resistance of the molded article can be significantly increased.

The molded article of the fourth example of the invention is the molded article of the third example of the invention, wherein the difference in the haze value of the molded article and the substrate is 1% or less.

In this way, in the case that the molded article is disposed on the surface of the image screen of for instance, an image display device, the surface of the image screen can be protected with the display of the image screen visible.

The image display device of the fifth example of the invention has: the molded article of the fourth example of the invention; and an image screen for which the molded article is disposed on a screen.

In this way, the surface of the image screen can be protected by the molded article for which the scratch resistance is significantly increased, and as a result the scratch resistance of the image display device can be significantly increased.

Effects of the Invention

The resin composition for a coating agent of the invention contains a silicon compound formed by modifying the two ends of a silicone compound by acrylic acid to achieve coating significantly increasing scratch resistance.

DESCRIPTION OF THE EXAMPLES

The present application is based on JP 2014-074664 submitted on Mar. 31, 2014 in Japan, and the content thereof is incorporated into the content of the present application. The invention can be better understood based on the following detailed descriptions. A further application range of the invention is shown by the following detailed descriptions. However, the detailed descriptions and specific examples are the ideal implementation of the invention and are only exemplary. The reason is that: those skilled in the art understand that various modifications and changes based on the detailed description are within the spirit and scope of the invention. The Applicant does not intend to publicize the recited implementations, and in the modified and substitute applications thereof, inventions not recited in the scope of the claims should also be considered as a portion of the equivalent invention.

In the following, implementations of the invention are described with reference to figures. Moreover, the same or similar reference numerals are used for the same or equivalent parts in each figure, and overlapping descriptions are omitted. Moreover, the invention is not limited to the following implementations.

[Silicon Compound (a)]

First, the silicon compound (a) included in the resin composition for a coating agent of the present application is described. The structure of the silicon compound (a) is as follows.

The silicon compound (a) is a compound containing a silicone chain (a siloxane bond as the main chain) and for which the two ends are modified by acrylic acid. Preferably, formula (III-2) contains the silicon compound (a) having a siloxane bond for which n=1. The (meth)acryloyl group having a functional group at two ends can be divided into, for instance, a difunctional acrylic-modified silicon compound, a tetrafunctional acrylic-modified silicon compound, and an octafunctional acrylic-modified silicon compound based on the number of functional groups.

Moreover, in the silicon compound (a), the acrylic acid equivalent is adjusted by changing the number of the (meth)acryloyl groups introduced in the silicon compound (a), so as to adjust the compatibility with the curable resin (b). Moreover, by changing the silicone chain without changing the number of the (meth)acryloyl group to adjust the acrylic acid equivalent, the compatibility of the silicon compound (a) to the curable resin (b) can also be adjusted, which is therefore preferred.

The structure of the skeleton of the silicon compound (a) is exemplified in formula (III-1). In formula (III-1), n is an integer of 1 to 20. The alkylene group ($-C_3H_6-$) is exemplary, and other alkylene groups can be included. X is a group having a (meth)acryloyl group. In X, $R_2$ is hydrogen or a methyl group.

Moreover, by setting n of the silicone bond to 1 to 20, the compatibility of the silicon compound (a) can be increased, and the haze value can be kept at a suitable value, which is therefore preferred.

[formula 3]

(III-1)

In the silicon compound (a), preferably, the silicon compound (a) having a siloxane bond for which n=1 is represented by formula (III-2). The silicon compound (a) can be mixed in the curable resin with good compatibility. $R_1$ is a $C_3$ or $C_4$ alkylene group. X is a group having a urethane skeleton and having a (meth)acryloyl group at the end. In X, $R_2$ is hydrogen or a methyl group, and n is an integer of 0 or 1.

[formula 4]

(III-2)

•Difunctional Acrylic-Modified Silicon Compound
X is a group of formula (IV).

(IV)

- Tetrafunctional Acrylic-Modified Silicon Compound

X is a group of formula (V) or formula (VI).

In formula (VI), Y is a group of formula (VII), formula (VIII), or formula (IX).

- Octafunctional Acrylic-Modified Silicon Compound

X is a group of formula (X).

(X)

(V)

(VI)

(VII)

(VIII)

(IX)

The calculated molecular weight of the silicon compound (a) is preferably in the range of 500 to 699. In that range, the compatibility of the silicon compound (a) can be increased, and the haze value can be kept below a suitable value.

The calculated molecular weight of the silicon compound (a) is, for instance, not lower than 533 and not greater than 677, but n in each molecule of each of $R_1$, $R_2$, formula (IV), and formula (V) is also sometimes different. In this case, the number-average molecular weight can also be measured. However, using gel permeation chromatography (GPC) when measuring number-average molecular weight may produce error in the molecular weight range.

In the following, a difunctional acrylic-modified silicon compound is shown as an example. In formula (III-2), $R_1$ is a $C_3$ alkylene group, X is formula (IV), $R_2$ is hydrogen, and n is 1. Next, a tetrafunctional acrylic-modified silicon compound is shown. In formula (III-2), $R_1$ is a $C_3$ alkylene group, X is formula (V), $R_2$ is hydrogen, and n is 1.

The synthesis method of the silicon compound (a) of the present application is exemplified below.

In the silicon compound (a), a hydroxyl-containing siloxane compound (such as Silaplane FM4401 made by JNC) is reacted with isocyanate having a (meth)acryloyl group such as acryloyloxy ethyl isocyanate (such as Karenz AOI made by Showa Denko) in the presence of a tin catalyst (such as dibutyltin dilaurate), so as to obtain a difunctional acrylic-modified silicon compound.

Alternatively, a hydroxyl-containing siloxane compound (such as Silaplane FM4401 made by JNC) is reacted with isocyanate having a (meth)acryloyl group such as 1,1'-(bisacryloyloxy methyl)ethyl isocyanate (such as Karenz BEI made by Showa Denko) in the presence of a tin catalyst (such as dibutyltin dilaurate), so as to obtain a tetrafunctional acrylic-modified silicon compound.

Alternatively, 1,1,3,3-tetramethyldisiloxane is reacted with, for instance, trimethylolpropane allyl ether in the presence of a platinum catalyst to obtain a two-end dihydroxyl-modified silicon compound.

Then, a two-end dihydroxyl-modified silicon compound is reacted with isocyanate having a (meth)acryloyl group such as 1,1'-(bisacryloyloxy methyl)ethyl isocyanate (such as Karenz BEI made by Showa Denko) in the presence of a tin catalyst (such as dibutyltin dilaurate), so as to obtain an octafunctional acrylic-modified silicon compound.

Moreover, the manufacturing method of the siloxane compound containing a hydroxyl group is as provided in JP 3661807.

Moreover, the catalyst used in the reaction of the two-end hydroxyl-modified silicon compound and the isocyanate having a (meth)acryloyl group can include, for instance: an amine catalyst (such as triethylenediamine), a carboxylate catalyst (such as lead naphthenate, potassium acetate), a trialkyl phosphine catalyst (such as triethylphosphine), a titanium catalyst (such as n-butyl dioxide).

[Resin Composition for Coating Agent]

The resin composition for a coating agent of the first example of the present application is a resin composition containing the acrylic-modified silicon compound (a). The resin composition for a coating agent of the present application can be easily prepared by adding the silicon compound (a) in a coating solution containing the curable resin (b). For instance, by adding, for instance, the silicon compound (a), an optional polymerization initiator suitable for the curable resin (b), and a solvent promoting mixing in a coating solution prepared by the method recited in JP 5375100, the resin composition for a coating agent of the present application can be obtained.

The solvent can include, for instance: an ether solvent (such as diethyl ether, tetrahydrofuran, diphenyl ether, anisole, dimethoxybenzene, propylene glycol monomethyl ether), a halogenated hydrocarbon solvent (such as dichloromethane, chloroform, chlorobenzene), a ketone solvent (such as acetone, methyl ethyl ketone, methyl isobutyl ketone), an alcohol solvent (such as methanol, ethanol, propanol, isopropanol, butanol, t-butanol), a nitrile solvent (such as acetonitrile, propionitrile, benzonitrile), an ester solvent (such as ethyl acetate, butyl acetate), a carbonate solvent (such as ethylene carbonate, propylene carbonate), an amide solvent (N,N-dimethylformamide, N,N-dimethylacetamide), a hydrochlorofluorocarbon solvent (HCFC-141b, HCFC-225), a hydrofluorocarbon (HFC) solvent (HFC having 2 to 4, 5, and 6 or more carbons), a perfluorocarbon solvent (perfluoropentane, perfluorohexane), a cycloaliphatic hydrofluorocarbon solvent (fluorocyclopentane, perfluorocyclobutane), an oxygen-containing fluorine solvent (fluoroether, fluoropolyether, fluoroketone, fluoroalcohol), an aromatic fluorine solvent (α,α,α-trifluorotoluene, hexafluorobenzene), water. The solvents can be used alone and can also be used in a combination of two or more.

In the case that the total of the silicon compound (a) and the curable resin (b) is set to 100 wt %, the silicon compound (a) is preferably 0.5 wt % to 40 wt %. The difunctional acrylic-based silicon compound is preferably 0.5 wt % or more and less than 20 wt %, more preferably 5 wt % to 10 wt %. The tetrafunctional acrylic-modified silicon compound is preferably 0.5 wt % to 30 wt %, and the octafunctional acrylic-modified silicon compound is preferably 0.5 wt % to 40 wt %. If the number of functional groups is increased, then solubility is increased, and therefore the amount can be increased.

•Curable Resin (b)

The curable resin (b) can include, for instance, active energy ray curable resin or a thermosetting resin. In terms of the ease of the curing method, an active energy ray curable resin is more preferred, in particular a UV curable resin.

Moreover, in the present specification, active energy ray refers to an energy ray capable of breaking down a compound generating active species to generate active species. The active energy ray can include, for instance: light energy ray such as visible light, UV, infrared, or radiation such as X-ray, α-ray, β-ray, γ-ray, electron beam. In particular, UV is preferred.

•Active Energy Ray Curable Resin

The active energy ray curable resin can include, for instance: a resin having an unsaturated bond capable of performing radical polymerization such as (meth)acrylic urethane resin, polyester (meth)acrylate resin, (meth)acrylate monomer, unsaturated polyester resin, epoxy (meth)acrylate resin. The resins can be used alone or a plurality of resins can be used in combination. In particular, (meth)acrylic urethane resin, polyester (meth)acrylate resin are preferred. (Meth)acrylic urethane resin can easily produce a tough coating due to the urethane structure, and can provide softness at the same time.

The (meth)acrylic urethane resin can include, for instance, an oligomer containing a radical polymerization unsaturated group, and the oligomer containing a radical polymerization unsaturated group can be obtained by reacting polyisocyanate and a polyhydroxyl compound or polyol, and then reacting a (meth)acrylic compound containing a hydroxyl group and an optional allyl ether compound containing a hydroxyl group.

Specific examples of the polyisocyanate can include, for instance: 2,4-tolylene diisocyanate and an isomer thereof, diphenyl methane diisocyanate, hexamethylene diisocyanate, hydrogenated xylylene diisocyanate, isophorone diisocyanate, xylylene diisocyanate, dicyclohexylmethane diisocyanate, naphthalene diisocyanate, triphenylmethane triisocyanate, Burnock D-750, Crisbon NK (made by Dainippon Ink and Chemicals), Desmodule L (made by Sumitomo Bayer Urethane), Coronate L (made by Nippon Polyurethane Industry), Takenate D102 (made by Mitsui Takeda Chemicals), Isonate 143L (made by Mitsubishi Chemical).

The polyhydroxy compound can include, for instance: polyether polyol, polyester polyol, polycarbonate polyol, polycaprolactone polyol, and can specifically include, for instance: glycerin-ethylene oxide adduct, glycerin-propylene oxide adduct, glycerin-tetrahydrofuran adduct, glycerin-ethylene oxide-propylene oxide adduct, trimethylol propane-ethylene oxide adduct, trimethylol propane-propylene oxide adduct, trimethylolpropane-tetrahydrofuran adduct, trimethylol propane-ethylene oxide-propylene oxide adduct, dipentaerythritol-ethylene oxide adduct, dipentaerythritol-propylene oxide adduct, dipentaerythritol-tetrahydrofuran adduct, dipentaerythritol-ethylene oxide-propylene oxide adduct.

Specific examples of the polyol can include, for instance: ethylene glycol, diethylene glycol, triethylene glycol, polyethylene glycol, propylene glycol, dipropylene glycol, polypropylene glycol, 2-methyl-1,3-propanediol, 1,3-butanediol, adduct of bisphenol A and propylene oxide or ethylene oxide, 1,2,3,4-tetrahydroxyl butane, glycerin, trimethylolpropane, 1,2-cyclohexanediol, 1,3-cyclohexanediol, 1,4-cyclohexanediol, p-xylene glycol, bicyclohexyl-4,4-diol, 2,6-decalin glycol, 2,7-decalin glycol.

The hydroxyl-containing (meth)acrylic compound is not particularly limited, and preferably contains hydroxyl-containing (meth)acrylate, and can specifically include, for instance: 2-hydroxyethyl (meth)acrylate, 2-hydroxypropyl (meth)acrylate, 3-hydroxybutyl (meth)acrylate, polyethylene glycol mono(meth)acrylate, polypropylene glycol mono(meth)acrylate, tris(hydroxyethyl)isocyanurate di(meth)acrylate, pentaerythritol tri(meth)acrylate.

The polyester (meth)acrylate resin can include, for instance: (1) (meth)acrylate obtained via reaction of an epoxy compound containing an α,β-unsaturated carboxylate group and a polyester having a terminal carboxyl group obtained from a saturated polyacid and/or an unsaturated polyacid and polyol; (2) (meth)acrylate obtained via reaction of a hydroxyl-containing acrylate and a polyester having a terminal carboxyl group obtained from a saturated polyacid and/or an unsaturated polyacid and polyol; (3) (meth)acrylate obtained via reaction of (meth)acrylic acid and a polyester having a terminal hydroxyl group obtained from a saturated polyacid and/or an unsaturated polyacid and polyol.

The saturated polyacid used as the raw material of polyester (meth)acrylate can include, for instance: polyacid without a polymerizable unsaturated bond or an anhydride thereof such as phthalic acid, isophthalic acid, terephthalic acid, tetrahydrophthalic acid, adipic acid, sebacic acid, and polymerizable unsaturated polyacid or an anhydride thereof such as fumaric acid, maleic acid, itaconic acid. Accordingly, the polyol component can include, for instance: ethylene glycol, propylene glycol, diethylene glycol, dipropylene glycol, 1,2-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, bisphenol A ethylene oxide adduct, bisphenol A propylene oxide adduct.

The (meth)acrylate monomer can include, for instance, compounds obtained by reacting α,β-unsaturated carboxylic acid and polyol. Examples can include, for instance: polyalkylene glycol di(meth)acrylate, ethylene glycol (meth)acrylate, propylene glycol (meth)acrylate, polyvinyl trimethylolpropane di(meth)acrylate, trimethylolpropane tri(meth)acrylate, trimethylolpropane ethoxy tri(meth)acrylate, trimethylolpropane diethoxy tri(meth)acrylate, trimethylolpropane triethoxy tri(meth)acrylate, trimethylolpropane tetraethoxy tri(meth)acrylate, trimethylol propane pentaethoxy tri(meth)acrylate, tetramethylol methane tetra(meth)acrylate, tetramethylol propane tetra(meth)acrylate, pentaerythritol tri(meth)acrylate, pentaerythritol tetra(meth)acrylate, pentaerythritol penta(meth)acrylate, dipentaerythritol penta(meth)acrylate, dipentaerythritol hexa(meth)acrylate.

The unsaturated polyester resin can include, for instance: a resin obtained by dissolving a condensation product (unsaturated polyester) obtained from the esterification reaction of polyol and unsaturated polyacid (and optional saturated polyacid) in a polymerizable monomer.

The unsaturated polyester can be formed from the condensation polymerization of unsaturated acid such as maleic anhydride and diol such as ethylene glycol. Specific examples can include, for instance: reacting polyacid having a polymerizable unsaturated bond or an anhydride thereof such as fumaric acid, maleic acid, itaconic acid as the acid component with polyol such as ethylene glycol, propylene glycol, diethylene glycol, dipropylene glycol, 1,2-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, bisphenol A ethylene oxide adduct, bisphenol A propylene oxide adduct as the alcohol component. Moreover, polyacid without a polymerizable unsaturated bond or an anhydride thereof such as phthalic acid, isophthalic acid, terephthalic acid, tetrahydrophthalic acid, adipic acid, sebacic acid is also added as needed as the acid component to form unsaturated polyester.

The epoxy (meth)acrylate resin can include, for instance: a resin obtained by dissolving a compound having a polymerizable unsaturated bond (vinyl ester) formed via the open-ring reaction of a compound having a glycidyl group (epoxy group) and a carboxylic group of a carboxylic compound having a polymerizable unsaturated bond such as acrylic acid in a polymerizable monomer.

The vinyl ester is formed by a known method, and can include, for instance, epoxy (meth)acrylate obtained by reacting unsaturated monobasic acid such as acrylic acid or methacrylic acid and epoxy resin.

Moreover, flexibility can also be provided by reacting various epoxy resins using bisphenol (such as A-type) or dibasic acid such as adipic acid, sebacic acid, dimer acid (Haridimer 270S: Harima Kasei).

The epoxy resin used as the raw material can include, for instance: bisphenol A diglycidyl ether and high-molecular weight homologues thereof, novolac glycidyl ether.

In the case that an active energy ray curable resin is used, a curing agent can be added as needed. In that case, based on the total of the active energy ray curable resin, the curing agent is preferably 0.1 wt % to 10 wt %, more preferably 0.1 wt % to 5 wt %, and still more preferably 0.1 wt % to 4 wt %. The curing agent can adopt an active energy ray polymerization initiator. The active energy ray polymerization initiator is not particularly limited as long as it is a compound generating radicals via the irradiation of active energy ray such as UV or visible light. The compound used as the active energy ray polymerization initiator includes, for instance: benzophenone, Michler's ketone, 4,4'-bis(diethylamino)benzophenone, xanthone, thioxanthone, isopropyl xanthone, 2,4-diethyl thioxanthone, 2-ethyl anthraquinone, acetophenone, 2-hydroxyl-2-methyl propiophenone, 2-hydroxyl-2-methyl-4'-isopropyl propiophenone, 1-hydroxyl cyclohexyl phenyl ketone, isopropyl benzoin ether, isobutyl benzoin ether, 2,2-diethoxyacetophenone, 2,2-dimethoxy-2-phenylacetophenone, camphorquinone, benzanthrone, 2-methyl-1-[4-(methylthio)phenyl]-2-morpholinopropan-1-one, 2-benzyl-2-dimethylamino-1-(4-morpholinophenyl)-butanone, ethyl 1,4-dimethyl aminobenzoate, isoamyl 4-dimethyl amino benzoate, 4,4'-di(t-butyl peroxy carbonyl) benzophenone, 3,4,4'-tri(t-butyl peroxy carbonyl) benzophenone, 2,4,6-trimethyl benzoyl diphenylphosphine oxide, 2-(4'-methoxystyryl)-4,6-bis(trichloromethyl)-s-triazine, 2-(3',4'-dimethoxystyryl)-4,6-bis(trichloromethyl)-s-triazine, 2-(2',4'-dimethoxystyryl)-4,6-bis(trichloromethyl)-s-triazine, 2-(2'-methoxystyryl)-4,6-bis(trichloromethyl)-s-triazine, 2-(4'-pentyloxystyryl)-4,6-bis(trichloromethyl)-s-triazine, 4[p-N,N-di(ethoxycarbonylmethyl)]-2,6-di(trichloromethyl)-s-triazine, 1,3-bis(trichloromethyl)-5-(2'-chlorophenyl)-s-triazine, 1,3-bis(trichloromethyl)-5-(4'-methoxyphenyl)-s-triazine, 2-(p-dimethylaminostyryl) benzoxazole, 2-(p-dimethylaminostyryl)benzothiazole, 2-mercaptobenzothiazole, 3,3'-carbonyl bis(7-diethylamino coumarin), 2-(o-chlorophenyl)-4,4',5,5'-tetraphenyl-1,2'-biimidazole, 2,2'-bis(2-chlorophenyl)-4,4',5,5'-tetrakis(4-ethoxycarbonyl phenyl)-1,2'-biimidazole, 2,2'-bis(2,4-dichlorophenyl)-4,4',5,5'-tetraphenyl-1,2'-biimidazole, 2,2'-bis(2,4-dibromophenyl)-4,4',5,5'-tetraphenyl-1,2'-biimidazole, 2,2'-bis(2,4,6-trichlorophenyl)-4,4',5,5'-tetraphenyl-1,2'-biimidazole, 3-(2-methyl-2-dimethylamino propionyl)carbazole, 3,6-bis(2-methyl-2-morpholino propionyl)-9-n-dodecyl carbazole, 1-hydroxycyclohexyl phenyl ketone, bis($\eta^5$-2,4-cyclopentadien-1-yl)-bis(2,6-difluoro-3-(1H-pyrrol-1-yl)-phenyl)titanium. The compounds can be used alone and can also be used in a combination of two or more. In particular, 3,3',4,4'-tetra(t-butyl peroxy carbonyl)benzophenone, 3,3',4,4'-tetra(t-hexyl peroxy carbonyl)benzophenone, 3,3'-di(methoxycarbonyl)-4,4'-di(t-butyl peroxy carbonyl)benzophenone, 3,4'-di(methoxycarbonyl)-4,3'-di(t-butyl peroxy carbonyl)benzophenone, 4,4'-di(methoxycarbonyl)-3,3-di(t-butyl peroxy carbonyl) benzophenone . . . etc. are preferred.

The activated energy ray curable resin can be cured by irradiating UV or electron beam via an active energy ray source.

As an example, the case in which UV is irradiated on the activated energy ray curable resin is described. The active energy ray curable resin is preferably cured by polymerization via the irradiation of UV in the presence of a photopolymerization initiator. The photopolymerization initiator can include, for instance: various benzoin derivatives, a benzophenone derivative, a phenyl ketone derivative, onium salt photoinitiator, an organometallic photoinitiator, a metal salt cationic photoinitiator, light-decomposable organosilane, latent sulfonic acid, phosphine oxide. Based on 100 parts by weight of the active energy ray curable resin, the amount of the photopolymerization initiator is preferably set to 1 part by weight to 5 parts by weight.

•Thermosetting Resin

The thermosetting resin can include, for instance: phenol resin, alkyd resin, melamine resin, epoxy resin, urea resin, unsaturated polyester resin, urethane resin, thermosetting polyimide, and silicone resin. The resins can be used alone or a plurality of resins can be used in combination.

Specifically, from the perspective of processability, epoxy resin such as bisphenol A epoxy resin, bisphenol F epoxy resin, polyfunctional epoxy resin, flexible epoxy resin, brominated epoxy resin, glycidyl ester epoxy resin, polymer epoxy resin, biphenyl epoxy resin, melamine resin such as methylated melamine resin, butylated melamine resin, methyl-etherified melamine resin, butyl-etherified melamine resin, methyl butyl mixed etherified melamine resin, urethane resin obtained by reacting a polyisocyanate compound having two or more isocyanate groups (O=C=N—R—N=C=O) and a polyol compound having two or more hydroxyl groups (HO—R'—OH), polyamine ($H_2N$—R"—$NH_2$) or compounds having active hydrogen (such as —$NH_2$, —NH—, —CONH—) such as water are preferred.

The heat resistance, adhesion, chemical resistance of the epoxy resin are excellent, the heat resistance, hardness, transparency of the melamine resin are excellent, the adhesion, low-temperature curability of the urethane resin are excellent, and therefore can be suitably selected for use.

The thermosetting resin needs to be rapidly cured at the desired curing temperature (80° C. to 160° C.) and time (30 seconds to 180 seconds). Based on the type of the resin, a curing reaction initiator or a curing reaction promoter can also be used. For instance, when the epoxy resin is used, the curing reaction initiator or the curing reaction promoter can include, for instance, amine such as aliphatic amine or aromatic amine, polyamide resin, tertiary amine and secondary amine, imidazole, polymercaptan, anhydride, Lewis acid complex, and when the melamine resin is used, the curing reaction initiator or the curing reaction promoter can include, for instance, sulfonic acid catalyst, and when the urethane resin is used, the curing reaction initiator or the curing reaction promoter can include, for instance, organometallic urethanization catalyst and tertiary amine urethanization catalyst.

The curing reaction initiator or curing reaction promoter only needs to be a compound releasing a substance triggering cationic polymerization via active energy ray irradiation or thermal energy. Examples of the curing reaction initiator include, for instance, carboxylic acid, amine, anhydride compound, or acid generator, and a complex salt of onium salt or a derivative thereof capable of releasing a Lewis acid is preferred.

A representative example of the curing reaction initiator can include, for instance, salts of the cation and the anion represented by formula (1).

$$[A]^{m+}[B]^{m-} \quad (1)$$

In formula (1), the cation $[A]^{m+}$ is preferably an onium ion, and is, for instance, represented by formula (2).

$$[(\alpha)_a Q]^{m+} \quad (2)$$

In formula (2), α is a $C_1$ to $C_{60}$ organic group and can contain several atoms other than carbon atoms. a is an integer of 1 to 5. An a number of α are respectively independent, and can be the same or different. Moreover, at least one α is preferably an organic group having an aromatic ring.

Q is an atom or an atom group selected from the group consisting of S, N, Se, Te, P, As, Sb, Bi, O, I, Br, Cl, F, and N=N. Moreover, when the atomic value of Q in the cation $[A]^{m+}$ is set to q, m=a-q (wherein N=N has an atomic value of 0).

Moreover, the anion $[B]^{m-}$ is preferably a halide complex such as formula (3).

$$[LX_b]^{m-} \quad (3)$$

In formula (3), L is a metal or metalloid used as the central atom of the halide complex, such as B, P, As, Sb, Fe, Sn, Bi, Al, Ca, In, Ti, Zn, Sc, V, Cr, Mn, Co. X is a halogen atom. b is an integer of 3 to 7. Moreover, when the atomic value of L in the anion $[LX_b]^{m-}$ is set to p, m=b-p.

Specific examples of the anion $[LX_b]^{m-}$ represented by formula (3) include, for instance: tetrafluoroborate ($BF_4$), hexafluorophosphate ($PF_6$), hexafluoroantimonate ($SbF_6$), hexafluoroarsenate ($AsF_6$), hexachoroantimonate ($SbCl_6$).

Moreover, the anion $[B]^{m-}$ can preferably include the anion represented by formula (4). L, X, and b are the same as above.

$$[LX^{b-1}(OH)]^{m-} \quad (4)$$

Examples of the anion $[B]^{m-}$ further include, for instance: perchlorate ion ($ClO_4^-$), trifluoromethyl sulfite ion ($CF_3SO_3^-$), fluorosulfonate ion ($FSO_3^-$), toluenesulfonic acid anion, trinitrobenzene sulfonate anion.

In such an onium salt, the curing reaction initiator of the invention is preferably the aromatic onium salt exemplified by (A) to (C). Among these, one can be used, or a combination of two or more can be used.

(A) Aryl diazonium salt such as phenyl diazonium hexafluorophosphate, 4-methoxyphenyl diazonium hexafluoroantimonate, 4-methylphenyl diazonium hexafluorophosphate.

(B) Diaryl iodonium salt such as diphenyliodonium hexafluoroantimonate, di(4-methylphenyl)iodonium hexafluorophosphate, di(4-t-butylphenyl)iodonium hexafluorophosphate.

(C) Triaryl sulfonium salt such as triphenylsulfonium hexafluoroantimonate, tris(4-methoxyphenyl)sulfonium hexafluorophosphate, diphenyl-4-thio-phenoxyphenyl sulfonium hexafluoroantimonate, diphenyl-4-thio-phenoxyphenyl sulfonium hexafluorophosphate, 4,4'-bis(diphenyl sulfonio)phenyl sulfide-bis-hexafluoroantimonate, 4,4'-bis(diphenyl sulfonio)phenyl sulfide-bis-hexafluorophosphate, 4,4'-bis[di(β-hydroxyethoxy)phenyl sulfonio]phenyl sulfide-bis-hexafluoroantimonate, 4,4'-bis[di(β-hydroxyethoxy)phenyl sulfonio]phenyl sulfide-bis-hexafluorophosphate, 4-[4'-(benzoyl)phenylthio]phenyl-di-(4-fluorophenyl)sulfonium hexafluoroantimonate, 4-[4'-(benzoyl)phenylthio]phenyl-di-(4-fluorophenyl)sulfonium hexafluorophosphate.

Accordingly, the curing initiator of the invention can also be a mixture of iron arene complex or aluminum complex, and a silanol such as triphenyl silanol.

Examples of the iron arene complex include, for instance, $(\eta^5$-2,4-cyclopentadien-1-yl)[(1,2,3,4,5,6-$\eta$)-(1-methyl ethyl)benzene]-iron-hexafluorophosphate, and examples of the aluminum complex include, for instance, tris(acetylacetonate)aluminum, tris(ethyl acetyl acetate)aluminum, tris (salicylaldehyde) aluminum.

Among these, from the perspective of practicality, the curing reaction initiator of an example of the invention is preferably aromatic iodonium salt, aromatic sulfonium salt, iron-arene complex.

Based on 10 moles to 300 moles of the epoxy group in the epoxy resin, the amount of the curing reaction initiator (preferably acid generator) is preferably 1 mole.

The curable resin layer preferably has weatherability, low index of refraction, high index of refraction, antifouling properties, low wear properties, gas barrier properties, scratch resistance based on the application. The following additives or methods can also be used to provide these properties.

The UV absorbent can include, for instance: benzotriazole, hydroxyphenyl triazine, benzophenone, salicylate, cyanoacrylate, triazine, or dibenzoyl resorcinol. The UV absorbents can be used alone and can also be used in multiple combinations. The type or combination of the UV absorbent is preferably suitably selected based on the wavelength of the UV to be absorbed.

The antioxidant can include: monophenol (such as 2,6-di-t-butyl-p-cresol, butylated hydroxyl anisole, 2,6-di-t-butyl-p-ethyl phenol, β-(3,5-di-t-butyl-4-hydroxyphenyl)propionic stearyl ester), bisphenol (such as 2,2'-methylenebis (4-methyl-6-t-butylphenol), 2,2'-methylenebis(4-ethyl-6-t-butylphenol), 4,4'-thiobis(3-methyl-6-t-butylphenol), 4,4'-butylidene bis(3-methyl-6-t-butylphenol), 3,9-bis[1,1-dimethyl-2-{β-(3-t-butyl-4-hydroxy-5-methylphenyl) propionyloxy}ethyl]2,4,8,10-tetraoxaspiro[5,5]undecane), polymer phenol (such as 1,1,3-tris(2-methyl-4-hydroxy-5-t-butylphenyl)butane, 1,3,5-trimethyl-2,4,6-tris(3,5-di-t-butyl-4-hydroxybenzyl)benzene, tetrakis-[methylene-3-(3',5'- di-t-butyl-4'-hydroxyphenyl)propionate]methane, bis[3,3'-bis-(4'-hydroxy-3'-t-butylphenyl)butyric acid]glycol ester, 1,3,5-tris(3',5'-di-t-butyl-4'-hydroxybenzyl)-s-triazine-2,4,6-(1H,3H,5H)trione, tocopherol), sulfur antioxidant (such as dilauryl 3,3'-thiodipropionate, dimyristyl 3,3'-thiodipropionate, distearyl 3,3'-thiodipropionate), phosphite (such as triphenyl phosphite, diphenyl isodecyl phosphite, phenyl diisodecyl phosphite, tris(nonylphenyl)phosphite, diisodecyl pentaerythritol phosphite, tris(2,4-di-t-butylphenyl) phosphite, cyclic neopentanetetrayl bis(octadecyl)phosphite, cyclic neopentanetetrayl bis(2,4-di-t-butylphenyl) phosphite, cyclic neopentanetetrayl bis(2,4-di-t-butyl-4-methylphenyl)phosphite, bis[2-t-butyl-6-methyl-4-{2-(octadecyl oxycarbonyl)ethyl}phenyl]hydrogen phosphite), and oxaphosphaphenanthreneoxide (such as 9,10-dihydro-9-oxa-10-phosphaphenanthrene-10-oxide, 10-(3,5-di-t-butyl-4-hydroxybenzyl)-9,10-dihydro-9-oxa-10-phosphaphenanthrene-10-oxide, 10-decyloxy-9,10-dihydro-9-oxa-10-phosphaphenanthrene-10-oxide). These antioxidants can respectively be used alone, and are preferably used in a combination of phenol/sulfur or phenol/phosphorous. Commercial phenol antioxidants can respectively include IRGANOX 1010 or IRGAFOS 168 made by BASF alone or in combination.

The light stabilizer (HALS) can include, for instance: TINUVIN (registered trademark) 5100 (neutral universal HALS), TINUVIN 292 (compounds: bis(1,2,2,6,6-pentamethyl-4-piperidyl)sebacate, methyl(1,2,2,6,6-pentamethyl-4-piperidyl)sebacate), TINUVIN 152 (compounds: 2,4-bis[N-butyl-N-(1-cyclohexyloxy-2,2,6,6-tetramethyl piperidine-4-yl)amino]-6-(2-hydroxyethyl amine)-1,3,5-triazine), TINUVIN 144 (compounds: bis(1,2,2,6,6-pentamethyl-4-piperidyl)-[[3,5-bis(1,1-dimethylethyl)-4-hydroxyphenyl]methyl]butyl malonate), TINUVIN 123 (compounds: sebacic acid, reaction product (in the presence of 1,1-dimethylethyl hydroperoxide and octane) of bis(2,2,6,6-tetramethyl-1-(octyloxy)-4: piperidyl)ester), TINUVIN 111FDL (about 50%, TINUVIN 622, compounds: (succinate polymer (4-hydroxyl-2,2,6,6-tetramethyl-piperidyl-yl) in the presence of ethanol); about 50%, CHIMASSORB 119, compounds: N-N'-N''—N'''-tetrakis(4,6-bis(butyl-(N-methyl-2,2,6,6-tetramethyl piperidine-4-yl)amino)triazin-2-yl)-4,7-diazadecane-1,10-diamine) made by BASF; or Adekastab LA series made by Adeka, specifically LA-52 ((5)-6116), LA-57((5)-5555), LA-62((5)-5711), LA-67((5)-5755). Moreover, the parenthesis contains the number of existing chemical substance.

The method of providing low index of refraction preferably includes mixing one or more of the following substances in the curable resin layer: inorganic fine particles such as magnesium fluoride, or a compound selected from the group consisting of fluorosilsesquioxane, fluorosilsesquioxane polymers recited in WO2008/072766 and WO2008/072765, or an acrylate compound containing a fluorine atom . . . etc.

The method of providing high index of refraction preferably includes mixing one or more of the following substances in the curable resin layer: a metal fine particle such as zirconium oxide, titanium oxide, zinc sulfide, an acrylate compound and an epoxy compound having a fluorene skeleton, or an acrylate compound and an epoxy compound containing a sulfur atom.

Transparent electrode material represented by indium tin oxide (ITO) or silver nanowires can be coated on the curable resin layer provided with high index of refraction, and patterning is performed via etching, such that a transparent electrode film in an electrostatic capacitive touch screen is formed. By using a curable resin layer provided with a high index of refraction, the conductive pattern of a transparent electrode material such as ITO or silver nanowires is not readily visible.

Moreover, by laminating a layer having low index of refraction on the curable resin layer provided with high index of refraction, the first curable resin layer having anti-reflective properties can be obtained.

In the method of providing antifouling properties or low friction properties, one or more compounds selected from the group consisting of a silicone compound, a fluorine compound, fluorosilsesquioxane, and fluorosilsesquioxane polymers recited in WO2008/072766 and WO2008/072765 are preferably mixed in the curable resin layer.

The silicone compound can include, for instance: BYK-UV3500 and BYK-UV-3570 (made by BYK Chemie), TEGO Rad2100, 2200N, 2250, 2500, 2600, 2700 (made by Degussa); X-22-2445, X-22-2455, X-22-2457, X-22-2458, X-22-2459, X-22-1602, X-22-1603, X-22-1615, X-22-1616, X-22-1618, X-22-1619, X-22-2404, X-22-2474, X-22-174DX, X-22-8201, X-22-2426, X-22-164A, X-22-164C (made by Shin-Etsu Chemical Co., Ltd.)

The fluorine compound can include, for instance: Optool DAC, Optool DAC-HP, R-1110, R-1210, R-1240, R-1620, R-1820, R-2020, R-5210, R-5410, R-5610, R-5810, R-7210, R-7310, Megafac RS-75, Megafac RS-72-K, Megafac RS-76-E, Megafac RS-76-NS, Megafac RS-77, Megafac RS-903-3, Megafac RS-914-2, Megafac RS-761-3 made by Daikin Industries Ltd.

The method of providing gas barrier properties preferably includes mixing one or more of an inorganic component such as layered clay or silicon dioxide, aluminum oxide, porous glass represented by graphene in the curable resin layer.

The method of providing scratch resistance can also include adding inorganic fine particles to increase surface hardness and scratch resistance of the cured film obtained by curing the resin composition for a coating agent of the present application. Specific examples of the inorganic fine particles can include, for instance: aluminum oxide, silicon oxide, rutile titanium dioxide, tin oxide, zirconium oxide, ceria, magnesium fluoride, ion oxide, zinc oxide, copper oxide, antimony oxide, cryolite, fluorite, apatite, calcite, plaster, and talc. Based on the curable resin (b) in the resin composition of the present application, the amount of the inorganic oxide is preferably less than 60 wt %. If less than 60 wt %, then good adhesion with the substrate can be maintained.

Moreover, the average particle size of the inorganic fine particles is preferably 5 nm to 2 μm, and if the transparency of the coating is considered, then is preferably 5 nm to 500 nm, more preferably 5 nm to 50 nm. In the case of 5 nm or more, the surface hardness and the scratch resistance of the cured film can be increased, and in the case of 2 μm or less, the transparency of the cured film is not negatively affected. Moreover, the average particle size of the inorganic fine particles was measured using Microtrac UPA made by Nikkiso via a dynamic light scattering method.

In addition, various additives such as active energy ray sensitizer, polymerization inhibitor, wax, plasticizer, leveling agent, surfactant, dispersant, defoamer, wettability improver, antistatic agent, curing additive can be added as needed.

If thermoplastic resin . . . etc. is mixed in the active energy ray curable resin or thermosetting resin, then the original properties (mechanical properties, surface/interface properties, compatibility . . . etc.) of the resin can be modified.

Examples of the thermoplastic resin include, for instance: polyethylene, polypropylene, polyvinyl chloride, polyvinylidene chloride, polystyrene, acrylonitrile-styrene resin, acrylonitrile-butadiene-styrene resin, poly(meth)acrylate resin, ultra-high molecular weight polyethylene, poly-4-methylpentene, syndiotactic polystyrene, polyamide (such as nylon 6: made by Dupont, nylon 6,6: made by Dupont, nylon 6,10: made by Dupont, nylon 6,T: made by Dupont, nylon MXD6: made by Dupont), polyester (such as polyethylene terephthalate, polybutylene terephthalate, polyethylene 2,6-naphthalene dicarboxylate), polyacetal, polycarbonate, polyphenylene oxide, fluorine resin (such as polytetrafluoroethylene, polyvinylidene fluoride), polyphenylene sulfide, polysulfone, polyether sulfone, polyether ether ketone, polyarylate (such as U polymer: made by Unitica, Vectra: made by Polyplastics), polyimide (such as Kapton: made by Toray, AURUM: made by Mitsui Chemicals), polyetherimide, and polyamide-imide.

[Molded Article]

The molded article of the second example of the invention is described. The molded article has a cured product obtained by curing the resin composition for a coating agent of the first example and a substrate covered by the cured product. Therefore, hard coating of the substrate surface can be achieved, and the scratch resistance of the substrate surface can be significantly increased, such that the substrate surface is protected from damage or contamination.

•Coating

The coating for the resin composition for a coating agent of the present application is preferably a wet coating method in which the composition is uniformly coated. The wet coating method can include, for instance, a gravure coating method or a die coating method. Moreover, the resin composition for a coating agent is preferably in a state suitable for coating, and can also not contain a solvent or a mixture containing a solvent.

The gravure coating method includes the following: dipping a gravure roll for which a convex and concave engraving process is performed on the surface in a coating solution, scarping off the coating solution adhered to the convex portion of the gravure roll surface using a doctor blade to accumulate the solution in the concave portion for a precise measurement, and then transferring to the substrate. Via the gravure coating method, a thin solution having low viscosity can be coated.

The die coating method includes applying pressure to extrude a solution from an ink head for coating referred to as the mold and coating at the same time. Via the die coating method, high-precision coating was achieved. Then, since the solution is not exposed to the atmosphere during coating, changes in concentration . . . etc. caused by drying do not readily occur.

Other wet coating methods can include, for instance: spin coating, bar coating, reverse coating, roll coating, slit coating, dip coating, spray coating, kiss coating, reverse kiss coating, air-knife coating, curtain coating, and rod coating. The coating method can be suitably selected from these methods based on the desired film thickness.

•Substrate

The substrate can include various transparent plastics or glasses. The transparent plastic material can include, for instance: resin such as polyester resin, acetate resin, polyether sulfone resin, polycarbonate resin, polyamide resin, polyimide resin, polyolefin resin, (meth)acrylic resin, polyvinyl chloride resin, polyvinylidene chloride resin, polystyrene resin, polyvinyl alcohol resin, polyarylate resin, polyphenylene sulfide resin, norbornene resin, cycloolefin resin, polyurethane resin. Specifically, polyethylene terephthalate (PET), polyethylene naphthalate, triacetyl cellulose, polyethersulfone, polycarbonate, polyacrylate, and polyether ether ketone are preferred. The cyclic olefin resin is preferably Zeonor (registered trademark), Zeonex (registered trademark): made by Zeon, Arton (registered trademark): made by JSR, Apel (registered trademark): made by Mitsui Chemicals, Topus (registered trademark): made by Polyplastics. Moreover, polyethylene terephthalate and polyethylene naphthalate are preferred due to excellent mechanical strength, dimensional stability, heat resistance, chemical resistance, and optical properties . . . etc. and surface smoothness or operability. Polycarbonate is preferred due to excellent transparency, impact resistance, heat resistance, dimensional stability, and flammability. If price and obtainability are considered, then polyethylene terephthalate is preferred. The transparent glass material is not particularly limited as long as a glass having excellent dimensional stability and optical properties for an LCD display or a touch screen . . . etc. is used. Examples can include, for instance: soda lime glass, alkali-free glass, alkaline barium glass, boron silicate glass, alkaline boron silicate glass, aluminum boron silicate glass, barium boron silicate glass, aluminum silicate glass, borate glass, silicon dioxide glass, lead glass.

The substrate can also be a substrate film for an optical protective film made by the material, and can also be a substrate for the display portion or touch screen portion of an electronic equipment such as PC, mobile terminal, GPS, liquid crystal display, and can also be a lens of, for instance, camera, glasses, goggles.

Moreover, the substrate of coating can also not be transparent, and can also be a frame of electronic equipment, electrical equipment, information technology (IT) related equipment. In this way, the substrate only needs to be hard-coated regardless of whether the substrate is transparent or not transparent.

•Thickness

The thickness of the substrate is not particularly limited and can be different based on the exemplified article. For instance, in the case of an optical protective film, the thickness of the substrate is preferably 50 μm to 300 μm, more preferably 80 μm to 200 μm. If the thickness of the substrate is 50 μm or more, then the mechanical strength of the substrate is sufficient, and a coating can be formed on the substrate. Moreover, if the thickness is 300 μm or less, then the thickness of the optical protective film is not too great, such that the product using the film (such as the image display device described later) is compact.

The thickness of the cured product of the resin composition for a coating agent formed on the substrate surface is also not particularly limited, and can be suitably changed based on the article exemplified.

•Haze Value

In the case that the cured product obtained by curing the resin composition for a coating agent is used in the image screen surface of an image display device . . . etc., preferably, the difference in haze value of the molded article (such as an optical protective film) having a substrate and a cured product and the haze value of just the substrate is 1% or less. That is, the following relationship of formula (5) is obtained. In the case of 1% or less, the display of the image screen can be identified without noticing the cured product at all.

$$|\text{haze value of molded article} - \text{haze value of substrate}| \leq 1\% \quad (5)$$

Moreover, the haze value is an indication relating to the transparency of the film and represents turbidity (haze). The haze can be obtained based on the ratio of diffusion transmitted light to total light transmitted light using formula (6). (Td: diffusion transmittance, Tt: total light transmittance)

Haze (%)=$Td/Tt$×100  (6)

[Image Display Device]

Figure 1:
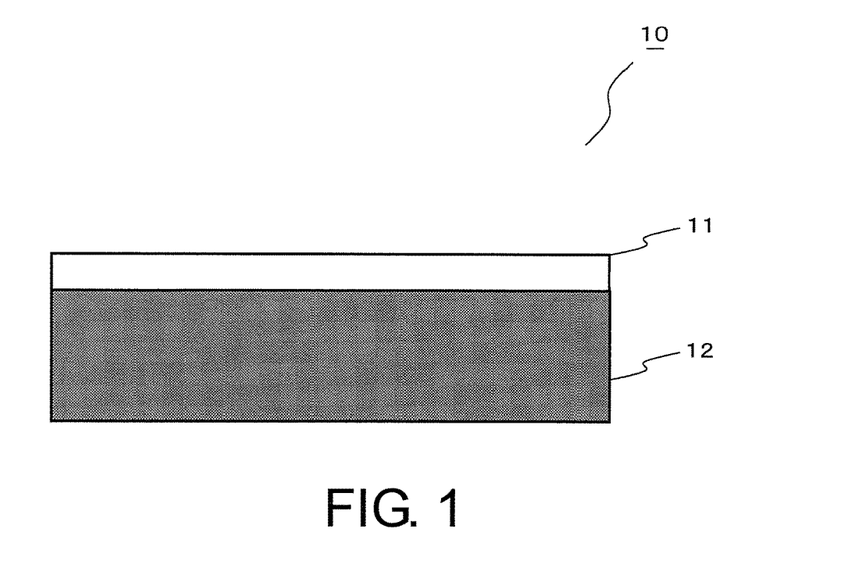
FIG. 1 exemplifies an image of an image display device of the third example of the invention.

The image display device 10 of the third example of the invention is described. As shown in FIG. 1, the image display device has the molded article (such as an optical protective film 11) of the second example and an image screen 12 displaying a projected image via mechanical processing. In the image screen 12, a flat panel display such as a cathode ray tube (CRT), a plasma display panel (PDP), or an LCD can be included. As shown in FIG. 1, the optical protective film 11 is mounted on the image screen 12 by placing the substrate of the optical protective film 11 in the bottom.

EXAMPLES

Synthesis Example 1

<Synthesis Example of Difunctional Acrylic-Modified Silicon Compound A>

A solution obtained by dissolving 0.47 g of dibutyltin dilaurate (made by Tokyo Kasei) in 4.7 g of methyl ethyl ketone (made by Wako Pure Chemical) was added in 250 g of two-end hydroxyl-modified silicon compound (Silaplane FM4401, hydroxyl equivalent: 173 g/mol, made by JNC), and the mixture was heated to 45° C. in a nitrogen atmosphere. 250.2 g of acryloyloxyethyl isocyanate (Karenz AOI, made by Showa Denko) was added dropwise in the solution, and stirring was performed at 45° C. to 50° C. for 2 hours. Next, a solution obtained by dissolving 0.23 g of dibutyltin dilaurate (made by Tokyo Kasei) in 2.3 g of methyl ethyl ketone (made by Wako Pure Chemical) was added, and stirring was performed at the same temperature for 2 hours. Next, the reaction solution was put in an ice bath to cool, and methanol (85.3 g) was added dropwise. Stirring was performed at the same temperature for 30 minutes to obtain the methanol solution of the difunctional acrylic-modified silicon compound A (594 g, solid content concentration: 77 wt %). The silicon compound A is shown below.

Synthesis Example 2

<Synthesis Example of Two-End Hydroxyl-Modified Silicon Compound B>

81.6 g of 2-allyloxy ethanol (made by Sigma-Aldrich) was added in 250 g of two-end dimethyl silyl polydimethylsiloxane (Silaplane FM1105, weight-average molecular weight: about 500, made by JNC), and the mixture was heated to 70° C. in a nitrogen atmosphere. 4 μl of a platinum catalyst xylene solution (PT-VTSC-3.0X, made by Umicore Japan, Pt content: 3 wt %) was added dropwise. 80.1 g of two-end dimethyl silyl polydimethylsiloxane (Silaplane FM1105, weight-average molecular weight: about 500, made by JNC) was added dropwise in a reaction system without exceeding 100° C. After stirring at 80° C. for 1 hour, the mixture was cooled to room temperature. Next, unreacted 2-allyloxy ethanol was removed via distillation under reduced pressure to obtain 130.4 g of the two-end hydroxyl-modified silicon compound B (yield: 93%). The silicon compound B is shown below.

[formula 13]

n = 5 ~ 8

Synthesis Example 3

<Synthesis Example of Difunctional Acrylic-Modified Silicon Compound C>

41.0 g of acryloyloxyethyl isocyanate (Karenz AOI, made by Showa Denko) was added in the two-end hydroxyl-modified silicon compound B (60.0 g), and the mixture was heated to 45° C. in a nitrogen atmosphere. A solution obtained by dissolving 0.076 g of dibutyltin dilaurate (made by Tokyo Kasei) in 0.55 g of methyl ethyl ketone (made by Wako Pure Chemical) was added dropwise, and stirring was performed at 45° C. to 50° C. for 2 hours. Next, a solution obtained by dissolving 0.043 g of dibutyltin dilaurate (made by Tokyo Kasei) in 0.54 g of methyl ethyl ketone (made by Wako Pure Chemical) was added, and stirring was performed at the same temperature for 2 hours. Next, the reaction solution was put in an ice bath to cool, and methanol (23.7 g) was added dropwise. Stirring was performed at the same temperature for 30 minutes to obtain the methanol solution of the difunctional acrylic-modified silicon compound C (116.5 g, solid content concentration: 81 wt %). The silicon compound C is shown below.

[formula 12]

[formula 14]

n = 5 ~ 8

Synthesis Example 4

<Synthesis Example of Difunctional Acrylic-Modified Silicon Compound D>

15.2 g of acryloyloxyethyl isocyanate (Karenz AOI made by Showa Denko) was added in 50.0 g of a two-end hydroxyl-modified silicon compound (Silaplane FM4411, hydroxyl equivalent: 564 g/mol, made by JNC), and the mixture was heated to 45° C. in a nitrogen atmosphere. A solution obtained by dissolving 0.028 g of dibutyltin dilaurate (made by Tokyo Kasei) in 0.83 g of Karenz AOI (made by Showa Denko) was added dropwise, and stirring was performed at 45° C. to 50° C. for 2 hours. Next, a solution obtained by dissolving 0.014 g of dibutyltin dilaurate (made by Tokyo Kasei) in 0.43 g of Karenz AOI (made by Showa Denko) was added, and stirring was performed at the same temperature for 2 hours. Next, the reaction solution was put in an ice bath to cool, and methanol was added dropwise (5.0 g). After stirring at the same temperature for 30 minutes, the mixture was heated to room temperature, and 50.0 g of methyl ethyl ketone (made by Wako Pure Chemical) was added. Methyl ethyl ketone solution of the difunctional acrylic-modified silicon compound D (121.3 g, solid content concentration: 54 wt %) was obtained. The silicon compound D is shown below.

acrylic-modified silicon compound A in the solid content was 5 wt %. Next, 0.50 g of Irgacure 127 (made by BASF) and 12.0 g of methyl isobutyl ketone (made by Wako Pure Chemical) were added such that the solid content concentration was 40 wt %. Stirring and mixing were performed until a transparent solution was obtained, and the solution was the coating solution 2.

Preparation Example 3

<Preparation of Coating Solution 3>
<Preparation of UV Resin Curing Agent 3>

25.9 g of methanol solution (solid content concentration: 77 wt %) of the difunctional acrylic-modified silicon compound A was added in 450.0 g of the coating solution 1 (solid content concentration: 40 wt %) prepared via the same method as preparation example 1, such that the difunctional acrylic-modified silicon compound A in the solid content was 10 wt %. Next, 1.0 g of Irgacure 127 (made by BASF) and 24.0 g of methyl isobutyl ketone (made by Wako Pure Chemical) were added such that the solid content concentration was 40 wt %. Stirring and mixing were performed until a transparent solution was obtained, and the solution was the coating solution 3.

n = 12 ~ 15

Preparation Example 1

<Preparation of Coating Solution 1>

A coating solution having a solid content concentration of 40 wt % was prepared by the method recited in JP 5375100. The resulting solution was the coating solution 1. The coating solution 1 had a solid content concentration of 40 wt %, and the composition in the solid content was 76 wt % of polyfunctional urethane acrylate, 19 wt % of inorganic filler, and 5 wt % of UV curing agent. Moreover, the coating solution 1 contained 0.2 wt % of antifouling additive (in liquid) and propylene glycol monomethyl ether (PGM)/isopropyl alcohol (IPA) used as dilution solvent.

Preparation Example 2

<Preparation of Coating Solution 2>

12.9 g of methanol solution (solid content concentration: 77 wt %) of the difunctional acrylic-modified silicon compound A was added in 475.0 g of the coating solution 1 (solid content concentration: 40 wt %) prepared via the same method as preparation example 1, such that the difunctional

Preparation Example 4

<Preparation of Coating Solution 4>

24.7 g of methanol solution (81 wt %) of the difunctional acrylic-modified silicon compound C was added in 450 g of the coating solution 1 (solid content concentration: 40 wt %) prepared via the same method as preparation example 1, such that the difunctional acrylic-modified silicon compound C in the solid content was 10 wt %. Next, 1.0 g of Irgacure 127 (made by BASF) and 25.3 g of methyl isobutyl ketone (made by Wako Pure Chemical) were added such that the solid content concentration was 40 wt %. Stirring and mixing were performed until a transparent solution was obtained, and the solution was the coating solution 4.

Preparation Example 5

<Preparation of Coating Solution 5>

37.0 g of methyl ethyl ketone solution (solid content concentration: 54 wt %) of the difunctional acrylic-modified silicon compound D was added in 450 g of the coating solution 1 (solid content concentration: 40 wt %) prepared via the same method as preparation example 1, such that the difunctional acrylic-modified silicon compound D in the solid content was 10 wt %. Next, 1.0 g of Irgacure 127 (made by BASF) and 13.1 g of methyl isobutyl ketone (made by Wako Pure Chemical) were added such that the solid content concentration was 40 wt %. Stirring and mixing were performed until a transparent solution was obtained, and the solution was the coating solution 5.

Example 1

<Forming of Curable Resin Layer 1>
Polycarbonate (Iupilon NF2000VU, size: 1.5 mm×70 mm×150 mm, made by Mitsubishi Gas Chemical) was used as the substrate. The coating solution 2 prepared in preparation example 2 was dip coated to the polycarbonate substrate. First, a polycarbonate substrate was vertically dipped in the coating solution 2 and then raised after dipping for 1 minute, and the polycarbonate substrate was raised vertically at a speed of 1 mm/s such that the dried film thickness was 5 μm. After drying at 80° C. for 1 minute, both surfaces of the coating were photocured using a high-pressure mercury lamp respectively under the light irradiation condition of 1000 mJ/cm$^2$ to form the curable resin layer 1.

Example 2

<Forming of Curable Resin Layer 2>
The curable resin layer 2 was formed via the same method used in example 1.
Except that the coating solution 3 prepared in preparation example 3 was used to replace the coating solution 2, the same method as example 1 was used to form the curable resin layer 2.

Example 3

<Forming of Curable Resin Layer 3>
The curable resin layer 3 was formed via the same method used in example 1.
Except that the coating solution 4 prepared in preparation example 4 was used to replace the coating solution 2, the same method as example 1 was used to form the curable resin layer 3.

Example 4

<Forming of Curable Resin Layer 4>
The curable resin layer 4 was formed via the same method used in example 1.
Except that the coating solution 5 prepared in preparation example 5 was used to replace the coating solution 2, the same method as example 1 was used to form the curable resin layer 4.

Comparative Example 1

<Forming of Curable Resin Layer 5>
The curable resin layer 5 was formed via the same method used in example 1.
Except that the coating solution 1 prepared in preparation example 1 was used to replace the coating solution 2, the same method as example 1 was used to form the curable resin layer 5.

<Coating Test>
(1) Total Light Transmittance
A haze meter (NDH5000, made by Nippon Denshoku Industries) was used to measure the curable resin layers. Implementation was performed based on the criteria of JIS-K-7361.
(2) Haze
A haze meter (NDH5000, made by Nippon Denshoku Industries) was used to measure the curable resin layers. Implementation was performed based on the criteria of JIS K 7136.
(3) Pencil Hardness
Measurement was performed on the curable resin layers based on JIS K 5600.
(4) Substrate Adhesion Test
11 tangents were respectively carved into the coating vertically and horizontally at 1 mm intervals to form 100 grids, and commercial cellophane tape (Sellotape (registered trademark), CT24, made by Nichiban) was sufficiently adhered to show the number of remaining grids of the coating not peeled during rapid peeling toward near the 90-degree direction. Moreover, the method was based on JIS K5400.
(5) Measurement of Contact Angle and Surface Free Energy (SFE)
Distilled water (for N/P measurement, made by Kanto Chemical) and tricresyl phosphate (99% (GC), made by Tokyo Chemical Industry) were used as probe liquids to measure contact angle, and surface free energy was calculated based on Kaelble-Uy theory.
(6) Steel Wool Wear Resistance Test
The wear resistance test machine "IMC-1557" made by Imoto Seisakusho was used. The measurement conditions were a vertical load of 1 kg, a reciprocating speed of 30 times/minute, a reciprocating distance of 100 mm, a reciprocating number of 1000, 5000, 10000, and the diameter of the wear cloth mount portion shape was 10 mm. Steel wool (#0000) was used as the wear cloth. The depth of the wear mark of the coating after a reciprocating number of 1000, 5000, and 10000 was measured. The difference between the contact portion and the non-contact portion of the wear cloth was measured using a contact difference meter "Alpha-step-IQ" made by KLA-Tencor as the wear mark depth.
The results of (1) to (6) are shown in Table 1.

TABLE 1

| | difunctional acrylic-modified silicon compound | | | | |
| --- | --- | --- | --- | --- | --- |
| | Example 1 | Example 2 | Example 3 | Example 4 | Comparative example 1 |
| Amount (wt %) | 5 | 10 | 10 | 10 | — |
| Silicone bond molecular weight | 100 | 100 | 500 | 1000 | — |
| Total light transmittance | 91 | 91 | 91 | 90 | 91 |
| Haze | 0.3 | 0.3 | 0.6 | 26 | 0.3 |
| Pencil hardness | B | B | B | B | HB |
| Substrate adhesion | 100/100 | 100/100 | 100/100 | 100/100 | 100/100 |

TABLE 1-continued

| difunctional acrylic-modified silicon compound | | | | | | |
|---|---|---|---|---|---|---|
| | | Example 1 | Example 2 | Example 3 | Example 4 | Comparative example 1 |
| Contact angle | H₂O | 100 | 100 | 97 | 96 | 97 |
| | Tricresyl phosphate | 63 | 63 | 61 | 62 | 63 |
| | SFE | 22 | 22 | 23 | 23 | 22 |
| Wear mark depth (nm) after steel wool wear test (10000 times) | | 200 | 200 | 830 | 1700 | 4300 |

Figures 2A, 2B:
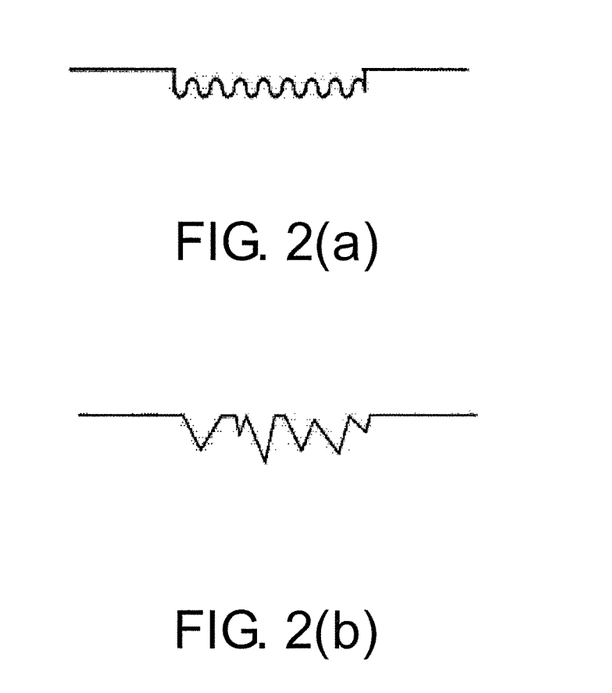
FIG. 2(a) is an image of wear marks of the examples.
FIG. 2(b) is an image of wear marks of the comparative examples.

If example 1 to example 4 (coating solutions with difunctional acrylic-modified silicon compounds) are compared with comparative example 1 (coating solution without a difunctional acrylic-modified silicon compound), then it is seen that the addition of the difunctional acrylic-modified silicon compound almost did not affect total light transmittance, substrate adhesion, SFE. Moreover, although the pencil hardness is slightly less, the wear mark depth in steel wool scratch resistance test is very shallow, and therefore the scratch resistance is significantly increased. Moreover, the shape of the wear mark was observed, and the results showed that, the wear mark of the examples was thin and was uniformly polished (FIG. 2(a)), and in comparison, the wear mark of the comparative examples was polished into an acute angle (FIG. 2(b)).

All literature containing the published objects, patent applications, and patents referenced in the present specification respectively and specifically show each literature and are incorporated by reference. In addition, all of the contents thereof are incorporated into the present specification by reference with the same limit described in the present specification.

If not particularly indicated in the present specification or not significantly contradictory to the wording, any term used in relation to the description (in particular relating to the following claims) and the use of similar terms of the invention are to be interpreted as singular and plural. The terms "have" and "contain" are interpreted as open scopes unless otherwise stated (i.e., "contains . . . but not limited to"). If not particularly indicated in the present specification, then the detailed description of numeric ranges in the present specification only functions as superficial description used to respectively mention each value in the range, and each value is incorporated into the specification by respectively providing examples in the present specification. If not particularly indicated in the present specification or not significantly contradictory to the wording, all of the methods described in the present specification can be performed in any suitable order. If not particularly claimed, all of the examples or exemplarily wordings (such as "etc.") used in the present specification are only intended to more sufficiently describe the invention, and do not limit the scope of the invention. The wordings int the specification should not be construed to represent elements not recited in the indispensable claims of the invention.

In the present specification, the most preferred configurations known to the Inventors are included, and preferred implementations of the invention are described. Those skilled in the art can understand the modifications to the preferred implementations after reviewing the descriptions. The Inventors predict those skilled in the art to suitably apply the modifications and to implement the invention using methods other than the ones specifically described in the present specification. Therefore, the invention includes all modifications and equivalents of the content recited in the accompanying claims of the present specification as accommodated by the Law. Therefore, any combination of the modified key elements not specifically indicated by the present specification or not significantly contradictory to the wording is also included in the invention.

What is claimed is:

1. A resin composition for a coating agent, comprising:
a silicon compound (a) represented by formula (I); and
a curable resin (b); and
in formula (I),
$R_1$ is a $C_3$ or $C_4$ alkylene group,
X is a group represented by formula (II) having a urethane skeleton and having a (meth)acryloyl group at an end,
in formula (II),
$R_2$ is hydrogen or a methyl group,
n is an integer of 0 or 1,
a molecular weight of the silicon compound (a) is 500 to 699, 2. The resin composition for a coating agent of claim 1, wherein the curable resin (b) is a UV curable resin having at least one (meth)acryloyl group.

3. A molded article, comprising:
a cured product formed by curing the resin composition for a coating agent of claim 1; and
a substrate covered by the cured product.

4. The molded article of claim 3, wherein a difference in a haze value of the molded article and the substrate is 1% or less.

5. An image display device, comprising:
the molded article of claim 4; and
an image screen for which the molded article is disposed on a screen.

* * * * *